United States Patent
Nakamura et al.

(10) Patent No.: US 6,683,222 B2
(45) Date of Patent: Jan. 27, 2004

(54) POLYETHER-POLYOL COMPOUND

(75) Inventors: Takeshi Nakamura, Yokkaichi (JP); Masatsugu Yamashita, Yokkaichi (JP)

(73) Assignee: Taiyo Kagaku Co., Ltd., Mie-ken (JP)

( * ) Notice: Subject to any disclaimer, the term of this patent is extended or adjusted under 35 U.S.C. 154(b) by 100 days.

(21) Appl. No.: 09/942,713

(22) Filed: Aug. 31, 2001

(65) Prior Publication Data

US 2002/0035238 A1 Mar. 21, 2002

(51) Int. Cl.[7] .............................................. C07C 43/11
(52) U.S. Cl. ...................................................... 568/606
(58) Field of Search ......................................... 568/606

(56) References Cited

FOREIGN PATENT DOCUMENTS

| JP | 62-210049 | 9/1987 |
| JP | 09-188755 | 7/1997 |

OTHER PUBLICATIONS

CA 75: 6834 abstract FR Patent 2017968.*
CA 75: 6834, FR patent 2017968.*

English Translation of Abstracts of Presentation at Academic Meeting for Nippon Yukagakukai in 1999 (38th Yukagaku Discussion), published Oct. 20, 1999, pp. 1–2.

* cited by examiner

Primary Examiner—Alan L. Rotman
Assistant Examiner—Hector M Reyes
(74) Attorney, Agent, or Firm—Birch, Stewart, Kolasch & Birch, LLP

(57) ABSTRACT

A polyether-polyol compound represented by the compositional formula $C_{3n}H_{6n+2}O_{2n+1}$, wherein n is an integer of 4 or more, wherein the polyether-polyol compound has a total number of 1,2-diol unit and 1,3-diol unit of $[(n/2)+1]$ in a case where n is an even number of 4 or more, or a total number of 1,2-diol unit and 1,3-diol unit of $[((n-1)/2)+1]$ and one hydroxyl group which is not involved in the units in a case where n is an odd number of 5 or more; a polyglycerol alkyl ether, a part of hydroxyl groups in a polyglycerol being substituted by an alkyl group, wherein the polyglycerol is the polyether polyol compound mentioned above; and an ester prepared by the process comprising reacting the polyether-polyol compound mentioned above or the polyglycerol alkyl ether mentioned above with a fatty acid.

8 Claims, No Drawings

POLYETHER-POLYOL COMPOUND

BACKGROUND OF THE INVENTION

1. Field of the Invention

The present invention relates to a polyether-polyol compound and a polyglycerol alkyl ether, an ester obtained by using the polyether-polyol compound or the polyglycerol alkyl ether, and a composition comprising the polyether-polyol compound, the polyglycerol alkyl ether or the ester.

2. Discussion of the Related Art

Conventionally, a polyether-polyol compound is prepared by carrying out an addition reaction of an alcohol with an epoxy compound, or a condensation reaction of a polyhydric alcohol at a high-temperature of 200° C. or more in the presence of a catalyst. The polyether-polyol compound formed by such reactions is mainly a linear compound. For instance, the structure of a polyglycerol, a kind of the polyether-polyol compound, can be generally represented as follows.

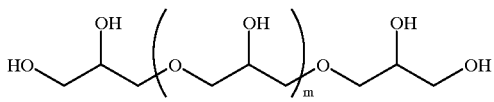

In the polyether-polyol compound having such a structure, as the degree of polymerization increases, the number of secondary hydroxyl group positioned in the inner part of the molecule increases, while the number of hydroxyl group positioned at a terminal of the molecule stays the time. The hydroxyl groups other than those at a terminal of this polyether-polyol compound have a low reactivity due to steric hindrance. Therefore, when the polyether-polyol compound is utilized, for instance, as a crosslinking agent for the resin, excess energy must be applied by such means of heating, thereby causing such problems as coloration.

In addition, the above-mentioned polyglycerol is esterified with a fatty acid to be mainly utilized as surfactants for foods. In the esterification, while the reaction rapidly progresses at a terminal hydroxyl group, the reaction is delayed at a central hydroxyl group. Therefore, especially severe conditions are required to prepare a lipophilic ester by adding a large amount of a fatty acid, thereby undesirably making the flavor and hue poor.

Nonionic surfactants can be utilized for a wide variety of purposes such as emulsification, solubilization, permeation, dispersion and washing. Widely used nonionic surfactants include glycerol fatty acid esters, sorbitan fatty acid esters, polyoxyethylene sorbitan fatty acid esters, polyethylene glycol fatty acid esters, polyoxyethylene alkyl ethers, polyoxyethylene alkylphenyl ethers, polyoxyethylene hardening castor oil derivatives, and the like. These nonionic surfactants can be classified into ester-type, ether-type and ester-ether-type by the binding modes of the lipophilic group moiety with the hydrophilic group moiety. Among them, ether-type surfactants are favorably utilized owing to their excellent stability against hydrolysis. As the hydrophilic group of the ether-type surfactant, polyoxyethylene is generally used. While the polyoxyethylene has an advantage of facilitation in the chain extension, there may arise such problems that harmful dioxane is formed during preparation, that formalin is generated by oxidation, and that the liquid becomes acidic.

In order to overcome the problems, ether-type surfactants having a polyglycerol having high safety as a hydrophilic group have been developed. For instance, Japanese Patent Laid-Open No. Sho 62-210049 discloses an ether obtained from di-, tri-, or tetraglycerol and a higher alcohol, and Japanese Patent Laid-Open No. Hei 9-188755 discloses a process for preparing a polyglycerol alkyl ether. However, conventional polyglycerols including those mentioned above have a linear structure, and they are composed of a mixture of polyglycerols having different degrees of polymerization. Therefore, a polyglycerol alkyl ether having a branched structure has not yet known.

Specifically, the conventionally known polyglycerol is a polyglycerol having a linear structure such as tetra-, hexa-, and decaglycerol, and its degree of polymerization is calculated on the basis of the hydroxyl value. Therefore, each polyglycerol does not mainly comprise tetra-, hexa-, and decamer of glycerol as indicated by its name, and each of them is composed of a mixture of polyglycerol comprising monomer to decal- or more 'mers of glycerol. When an alkyl ether is prepared by using the conventional polyglycerol, the resulting product would undesirably be composed of a mixture of various kinds of alkyl ethers. In addition, an alternative process for preparing a polyglycerol alkyl ether includes a process comprising carrying out a condensation reaction of glycidol or epichlorohydrin with an aliphatic alcohol. However, the degree of condensation of the resulting polyglycerol is adjusted by the amount of glycidol or epichlorohydrin added, so that one composed of a single degree of condensation cannot be obtained. The resulting polyglycerol alkyl ether obtained by these processes is composed of a mixture of components having different glycerol chain lengths, so that the compound does not exhibit the function inherently owned by the polyglycerol alkyl ether, rendering it necessary to use a large amount of the polyglycerol alkyl ether to achieve its purpose.

On the other hand, a polyglycerol fatty acid ester is a nonionic surfactant having high safety which is approved as a food additive, and is widely used in fields other than foods such as cosmetics and detergents. A polyglycerol which is used as a raw material for the presently commercially available polyglycerol fatty acid ester is prepared by polymerizing a glycerol-related compound such as glycerol, glycidol or epichlorohydrin. The polyglycerol formed by this reaction is a linear polyglycerol as mentioned above, and this linear polyglycerol is used in the preparation of the linear fatty acid ester by means of esterification with a fatty acid ester, which the resulting ester is presently used as a surfactant.

Generally, the shape of the hydrophilic moiety of the hydrophilic surfactant has a large effect on its performance. In order that the surfactant exhibits its effects, the surfactant must be adsorbed to the interface and cover its entire surface. In the polyglycerol fatty acid ester having linear polyglycerol moiety represented by the formula mentioned above as a hydrophilic group, the ester also takes a linear form. When the ester adsorbs to the interface, the area occupied by the adsorbed portion is a small value, approximating the cross-sectional area of the ester. Therefore, in order to exhibit its surfactant ability sufficiently, the interface must be covered completely, thereby consuming a large amount of a surfactant. Consequently, lowering of product values such as causing roughened skin when applied to cosmetics, and impairing flavors when applied to foods.

An object of the present invention is to provide a novel polyether-polyol compound, a polyglycerol alkyl ether and an ester having excellent emulsification, solubilization, dispersion, detergency, foaming strength or the like, of a polyglycerol, and a composition comprising the polyether-polyol compound, the polyglycerol alkyl ether or the ester.

These and other objects of the present invention will be apparent from the following description.

SUMMARY OF THE INVENTION

According to the present invention, there are provided:

(1) a polyether-polyol compound represented by the compositional formula:

$$C_{3n}H_{6n+2}O_{2n+},$$

wherein n is an integer of 4 or more,
wherein the polyether-polyol compound has a total number of 1,2-diol unit and 1,3-diol unit of [(n/2)+1] in a case where n is an even number of 4 or more, or a total number of 1,2-diol unit and 1,3-diol unit of [((n−1)/2)+1] and one hydroxyl group which is not involved in the units in a case where n is an odd number of 5 or more;
(2) a polyglycerol alkyl ether, a part of hydroxyl groups in a polyglycerol being substituted by an alkyl group, wherein the polyglycerol is the polyether polyol compound of item (1) above;
(3) an ester prepared by the process comprising reacting the polyether-polyol compound of item (1) above or the polyglycerol alkyl ether of item (2) above with a fatty acid; and
(4) a composition comprising the polyether-polyol compound of item (1) above, the polyglycerol alkyl ether of item (2) above, or the ester of item (3) above.

DETAILED DESCRIPTION OF THE INVENTION

The polyether-polyol compound of the present invention is a compound represented by the compositional formula:

$$C_{3n}H_{6n+2}O_{2n+1},$$

wherein n is an integer of 4 or more,
wherein the polyether-polyol compound has a total number of 1,2-diol unit and 1,3-diol unit of [(n/2)+1] in a case where n is an even number of 4 or more, or a total number of 1,2-diol unit and 1,3-diol unit of [((n−1)/2)+1] and one hydroxyl group which is not involved in the units in a case where n is an odd number of 5 or more. The polyether-polyol does not have a functional group containing oxygen atom other than the alcoholic hydroxyl group and ether bond.

The compositional formula of the polyether-polyol compound of the present invention can be confirmed by performing elemental analysis. Conveniently, the present compound can be applied on high-resolution mass spectrometer, to give its compositional formula.

In the present invention, the term "1,2-diol unit" refers to a structure in which two carbon atoms each having one hydroxyl group are directly bonded, and the "1,3-diol unit" refers to a structure in which two carbon atoms each having one hydroxyl group are bonded via one carbon atom having no hydroxyl group.

The polyether-polyol compound of the present invention has a total number of 1,2-diol unit and 1,3-diol unit of [(n/2)+1] in a case where n is an even number of 4 or more. This structure can be confirmed by subjecting the hydroxyl group existed on the adjoining carbon atoms to a specified reaction. For instance, 1,2-diol unit can be confirmed as follows. The present compound is reacted with a given amount of periodic acid, thereafter potassium iodide is added to the reaction mixture, and the formed iodine is titrated with a sodium thiosulfate solution to determine the consumed periodic acid. The found value is then compared with the theoretical value. In addition, as a specific reaction for partial structures of 1,2-diol unit and 1,3-diol unit, absorption of hydroxyl group cannot be found when the infrared absorption spectrum of the acetal of the polyether-polyol is determined, the acetal being obtained by reacting the present polyether-polyol compound with a compound having carbonyl group, such as acetone, methyl ethyl ketone or diethyl ketone, in the presence of a catalyst. Further, this acetal is applied on high-resolution mass spectrometer, whereby the resulting compound can be confirmed to be the polyether-polyol compound of the present invention by comparing the resulting compositional formula with the theoretical compositional formula.

In addition, the polyether-polyol compound of the present invention has a total number of 1,2-diol unit and 1,3-diol unit of [((n−1)/2)+1] and one hydroxyl group which is not involved in any of the units in a case where n is an odd number of 5 or more. The structure can be confirmed by the following method. Specifically, the present polyether-polyol compound is reacted with acetone in the presence of a catalyst, and the molecular weight of the resulting acetal of the polyether-polyol compound is determined, whereby the total number of 1,2-diol unit and 1,3-diol unit can be confirmed. Next, when the acetal is acetylated with acetic acid anhydride and pyridine to determine its molecular weight, the molecular weight increased by 42 as compared to that before acetylation. Each of the acetal and the resulting acetylated product is applied on high-resolution mass spectrometer, whereby the structure of the compound of the present invention can be confirmed more accurately by comparing the resulting compositional formula with the theoretical compositional formula.

The structure of the polyether-polyol of the present invention are exemplified as follows, without being limited to those exemplified.

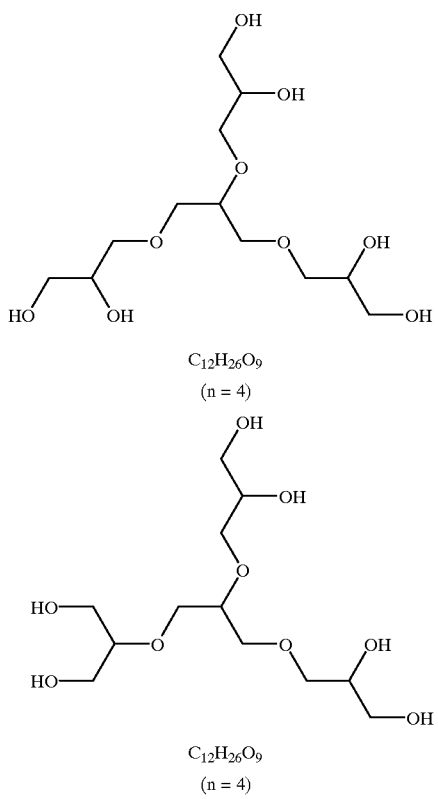

$C_{12}H_{26}O_9$ (n = 4)

$C_{12}H_{26}O_9$ (n = 4)

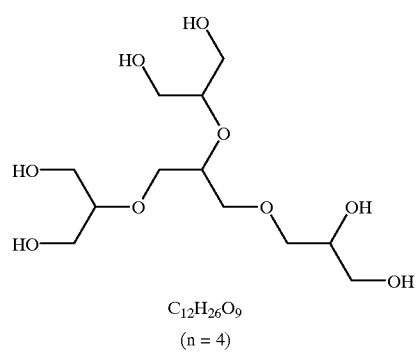
$C_{12}H_{26}O_9$
(n = 4)
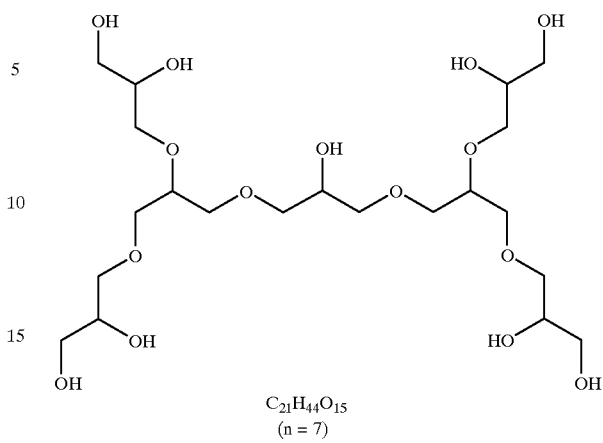
$C_{21}H_{44}O_{15}$
(n = 7)
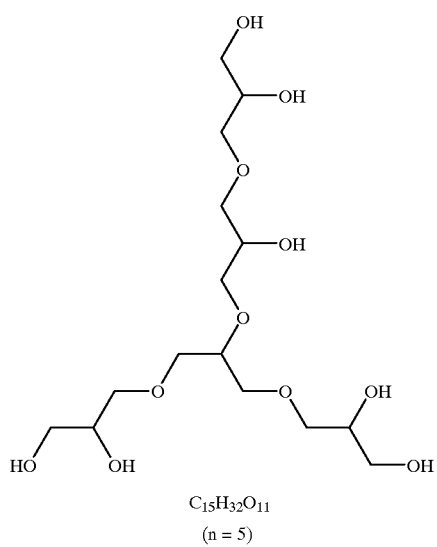
$C_{15}H_{32}O_{11}$
(n = 5)
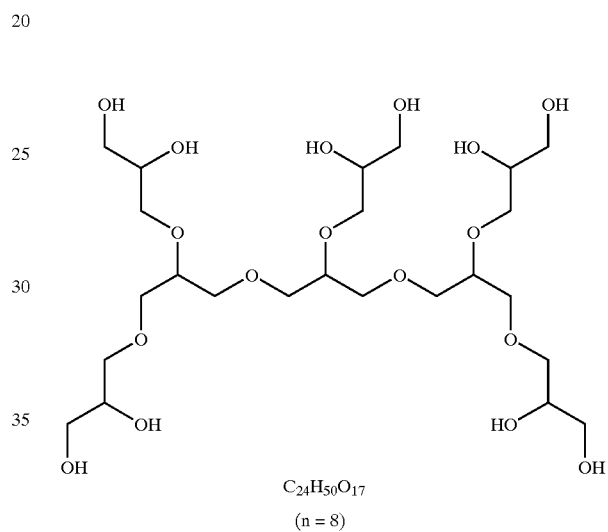
$C_{24}H_{50}O_{17}$
(n = 8)
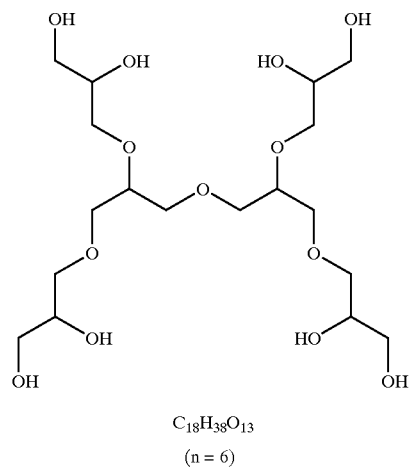
$C_{18}H_{38}O_{13}$
(n = 6)
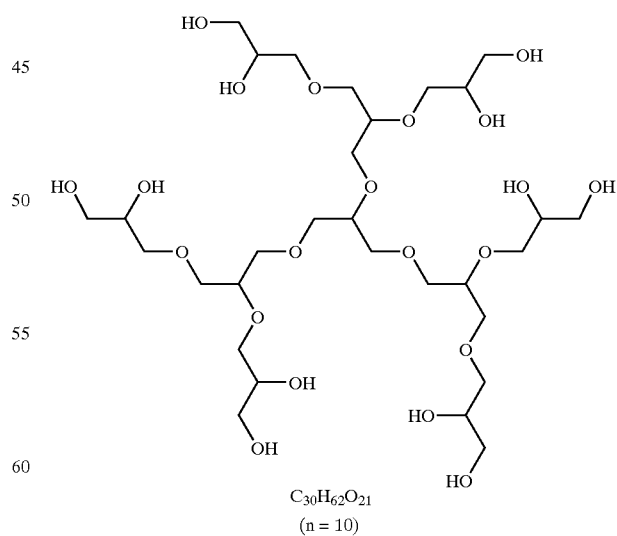
$C_{30}H_{62}O_{21}$
(n = 10)

-continued

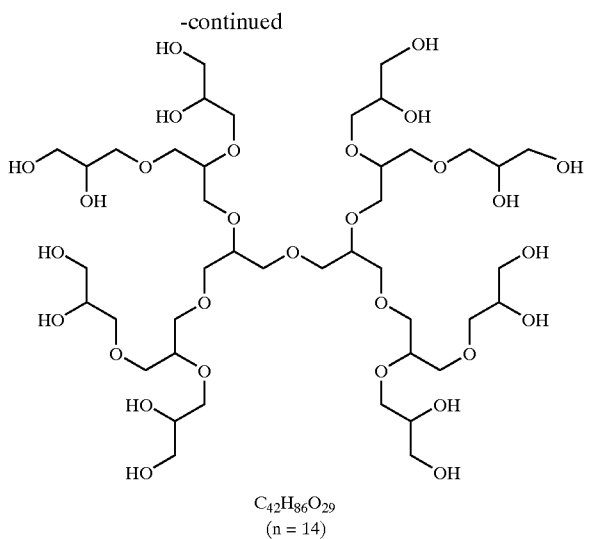

C₄₂H₈₆O₂₉
(n = 14)

The process for synthesizing the compound of the present invention is not particularly limited. For instance, the compound can be prepared by polymerizing a raw material polyhydric alcohol such as glycerol or a corresponding epoxide compound thereof with heating in the presence of a catalyst, thereafter reacting the product with a carbonyl group-containing compound such as acetone to give an acetal, purifying the desired product by separation distillation, and decomposing the acetal. Concretely, the compound of the present invention can be prepared by carrying out an addition reaction of epichlorohydrin to a glycerol or a polyglycerol having a degree of polymerization of 2 or more, such as diglycerol, to give an epoxide, and subjecting the epoxide to a ring-opening reaction. Alternatively, the compound of the present invention can be prepared by the steps of carrying out an addition reaction of an allyl halide with glycerol or a polyglycerol having a degree of polymerization of two or more to give an allyl ether compound, and carrying out a reaction for converting a double bond contained in allyl group of the allyl ether compound to a single bond to introduce two hydroxyl groups. Among the above processes, the latter process is more preferable. In addition, by repeating this reaction, the polyether-polyol compound having an even larger molecular weight can also be prepared.

In the present invention, a first step for preparation of the polyether-polyol compound comprises etherifying glycerol or a glycerol derivative with an allyl halide. The etherification can be carried out by a known method, and is not limited to a particular method. In this step, since all of hydroxyl groups of the glycerol or glycerol derivative are subjected to allyl-etherification, it is desired that the allyl halide is used in an amount equimolar to the glycerol or glycerol derivative. It is preferable that the amount of the allyl halide is from 1.5- to 5-folds by mol, preferably from 2- to 3-folds by mol, to the number of hydroxyl groups of the raw material glycerol or glycerol derivative.

As the allyl halide, allyl chloride, allyl bromide, allyl iodide, or the like can be utilized, and the allyl chloride and the allyl bromide are desired from the economic viewpoint.

The reaction can proceed at room temperature, and heating can be applied to the reaction in order to further increase efficiency. In this case, the upper limit of the heating temperature is determined by the boiling point of the allyl halide used. In addition, since the efficiency is markedly lowered in any of the allyl halide because the reactivity is lowered when the reaction temperature is low, it is preferable that the reaction temperature is from 10° to 45° C., preferably from 30° to 45° C. in a case of the allyl chloride, that the reaction temperature is from 10° to 71° C., preferably from 30° to 71° C. in a case of the allyl bromide, and that the reaction temperature is from 10° to 103° C., preferably from 30° to 103° C. in a case of the allyl iodide.

In this reaction, the reaction rate can be increased by adding a base or a catalyst. The base or catalyst includes alkali metals and alkaline earth metals; oxides, hydrides, hydroxides, and carbonates of these metals; organic basic compounds such as triethylamine; metals or metal oxides such as silver oxide and copper powder, without being limited thereto. Especially when the alkali metal hydroxide is used, the alkali metal hydroxide may be mixed with a glycerol derivative and thermally dehydrated to give an alkoxide, and the alkoxide is then reacted with the allyl halide.

Further, in order to efficiently progress the reaction, a solvent can be used. The solvent includes water, dimethyl sulfoxide, dimethyl formamide, dimethyl ether, tetrahydrofuran, dioxane, and the like, without being limited thereto. The amount of the solvent is not particularly limited, and it is preferably from about equivolume to about 5-folds the amount of the other raw materials.

In order to increase the purity of the final product, it is desired that a purification procedure is carried out after the termination of the allyl etherification reaction. For instance, the unreacted raw material glycerol or glycerol derivative, an unnecessary product having a low degree of etherification, an excess base or catalyst, a salt formed by the reaction or the like can be removed by washing the allyl ether compound with water. In addition, an excess allyl halide can be removed by heating the reaction mixture to a temperature equal to or higher than the boiling point of the allyl halide used, and the allyl halide can be even more efficiently removed under reduced pressure. Further, in order to improve the purity of the desired ether compound, the allyl ether compound itself can be purified by distillation with heating under normal pressure or reduced pressure. In addition, the desired ether compound can be purified by utilizing column chromatography using an adsorbent such as silica gel or alumina or a separating agent such as ion-exchanged resin, or distribution using an organic solvent.

In this allyl etherification reaction, it is desired that all of the hydroxyl groups of the raw material glycerol or glycerol derivative disappear at the termination point of the reaction. Since the allyl-etherified glycerol derivative has a dramatically lowered polarity, it can be readily confirmed by thin layer chromatography. In addition, the disappearance of the absorbance of hydroxyl group can be confirmed by infrared absorption spectrum. In a case where unreacted hydroxyl group exists in the resulting allyl ether compound obtained after the reaction and its subsequent purification, the resulting allyl ether compound can be reacted again with the allyl halide.

Hydroxyl group can be introduced into the allyl etherified derivative by a known process, and this process is not particularly limited. Examples of the process includes, for instance, a process comprising introducing a halogen such as chlorine or bromine, or a halohydrin, and hydrolyzing the product, thereby introducing hydroxyl group; or a process of introducing hydroxyl group via an epoxide. In general, a double bond is formed into an epoxide, and thereafter subjecting the epoxide to a ring-opening reaction with an acid or alkali to introduce hydroxyl group. In this epoxidation, a peracid is generally employed. The peracid includes peracetic acid, performic acid, pertrifluoroacetic acid and the like, which are usually prepared by adding an aqueous hydrogen peroxide to a corresponding acid. Besides, an organic peracid such as metachloroperbenzoic acid, orthosulfoperbenzoic acid, peroxyphthalic acid, monoperoxysuccinic acid or disuccinoyl peroxide can be utilized. Further, an oxidizing agent such as potassium permanganate or osmium tetraoxide can be utilized.

In the epoxidation step, the reaction can be carried out at 10° to 100° C. When the temperature is low, the reactivity is low, and when the temperature is high, the formed epoxide compounds are polymerized with each other, so that the purity of the reaction product is lowered. The reaction can be preferably achieved at a temperature of from 30° to 50° C.

This epoxide compound is subsequently hydrolyzed, and hydroxyl group is introduced, to give a polyglycerol or polyglycerol derivative. The epoxide compound is hydrolyzed with an acid or aqueous alkali solution, desirably with an aqueous sodium hydroxide or an aqueous potassium hydroxide. The reaction can be preferably achieved at a temperature of from 20° to 60° C., preferably from 40° to 50° C. During the process, when the reaction temperature is low, the reactivity is low, and when the temperature is high, the formed epoxide compounds are polymerized with each other, so that the purity of the reaction product is lowered. After a major part of the epoxide compound is decomposed, the reaction mixture can be finally heated to a temperature of 100° C. or higher, and refluxed with heating in order to complete the reaction.

In addition, this epoxide compound can be reacted with hydroxyl group of glycerol or a glycerol derivative, to give a polyglycerol or polyglycerol derivative. In this case, the reaction proceeds without a catalyst, but a catalyst can be used. The basic catalyst includes hydroxides and alcholates of alkali metals and alkaline earth metals, and organic basic compounds. The acidic catalyst includes protonic acids such as hydrochloric acid, sulfuric acid, nitric acid, and phosphoric acid; Lewis acids such as boron trifluoride and aluminum chloride; and organic acids such as formic acid and acetic acid, without being limited thereto. It is preferable that the reaction temperature is from 40° to 250° C., preferably from 70° to 150° C. When the reaction temperature is less than 40° C., too much time is consumed before the termination of the reaction, thereby making its efficiency poor, and when the reaction temperature exceeds 250° C., the decomposition of the epoxide undesirably takes place.

In the polyglycerol or polyglycerol derivative (hereinafter simply referred to as "reaction product") obtained by these processes, the raw materials used in epoxidation and hydrolysis and by-product salts formed during the process can be contained. These raw materials and by-product salts can be removed by distilling off low-molecular compounds under normal pressure or reduced pressure, or by using an ion-exchanging resin. Further, the reaction product can be purified by a known means utilizing molecular distillation or chromatographic apparatus. The purity of the polyglycerol or polyglycerol derivative thus obtained can be determined by an analytical means such as gas chromatography or liquid chromatography described above.

In the process described above, a polyglycerol comprising a glycerol polymer having a single degree of polymerization in a high purity can be efficiently prepared. The high-purity polyglycerol in the present invention is not particularly limited. For instance, when subjected to previously mentioned gas chromatography or liquid chromatography, it is desired that the purity of the single component is 60% by area or more, preferably 70% by area or more, more preferably 80% by area or more.

In addition, as the glycerol derivative, the glycerol bone structure can be extended by following the same procedures as above. The polyglycerol derivative consequently obtained can be used as a polyglycerol by removing the introduced substituent, or the polyglycerol derivative per se can be utilized with the substituent. For instance, the polyglycerol alkyl ether per se obtained from a raw material glycerol alkyl ether can be utilized as a hydrophilic surfactant. In this case, not only the hydrophilic moiety has an evenly sized degree of polymerization of glycerol, but also the monoalkyl ether only can be efficiently obtained.

Alternatively, the polyether-polyol compound can also be synthesized by carrying out an addition polymerization of a commercially available linear polyglycerol obtained by polymerizing glycerol or an epoxide compound, with the allyl halide, to give an allyl ether compound; and carrying out a reaction for converting a double bond contained in allyl group of the allyl ether compound to a single bond to introduce two hydroxyl groups. In this case, since the resulting product is composed of a mixture of the polyether-polyol having different degrees of polymerization, the gas chromatography mass spectrometer (GC—MS) or the liquid chromatography mass spectrometer (LC—MS) is preferred as its analysis or structural confirmation. Specifically, the polyether-polyol compound can be identified by forming the compound into an acetal, acetylating the acetal, lying the acetylated compound on GC—MS or LC—MS to determine its molecular weight at each peak, and comparing the found values with those of the theoretical values. Further, if the composition is determined by subjecting each peak to a higher resolution mass spectroscopy, its determination can be made more accurately. A part of the molecular weights of the branched polyglycerol with its degree of polymerization and compositional formula, the branched polyglycerol formed into an acetal with acetone, and those acetylated products after acetal formation is shown in Table 1.

TABLE 1

| Degree of Polymerization | Compositional Formula | Molecular Weight | | |
|---|---|---|---|---|
| | | Before Treatment | Acetal Formation | Acetylated After Acetal Formation |
| 4 | $C_{12}H_{26}O_9$ | 314 | 434 | 434 |
| 5 | $C_{15}H_{32}O_{11}$ | 388 | 508 | 550 |
| 6 | $C_{18}H_{38}O_{13}$ | 462 | 622 | 622 |
| 7 | $C_{21}H_{44}O_{15}$ | 536 | 696 | 738 |
| 8 | $C_{24}H_{50}O_{17}$ | 610 | 810 | 810 |
| 9 | $C_{27}H_{56}O_{19}$ | 684 | 884 | 926 |
| 10 | $C_{30}H_{62}O_{21}$ | 758 | 998 | 998 |
| 11 | $C_{33}H_{68}O_{23}$ | 832 | 1072 | 1114 |
| 12 | $C_{36}H_{74}O_{25}$ | 906 | 1186 | 1186 |
| 13 | $C_{39}H_{80}O_{27}$ | 980 | 1260 | 1302 |
| 14 | $C_{42}H_{86}O_{29}$ | 1054 | 1374 | 1374 |
| 15 | $C_{45}H_{92}O_{31}$ | 1128 | 1448 | 1490 |

In the polyglycerol alkyl ether of the present invention, a part of hydroxyl groups in a polyglycerol is substituted by an alkyl group, wherein the polyglycerol is the polyether polyol compound of the present invention.

The term "polyglycerol" used herein refers to a compound which is regarded to be prepared by dehydrating glycerol molecules and polymerizing them, namely a compound comprising four or more consecutive units, and is represented by the compositional formula:

$$C_{3n}H_{6n+2}O_{2n+1},$$

wherein n is an integer of 4 or more.

The structures which are taken by the polyglycerol alkyl ether of the present invention are exemplified as follows, without being limited thereto.

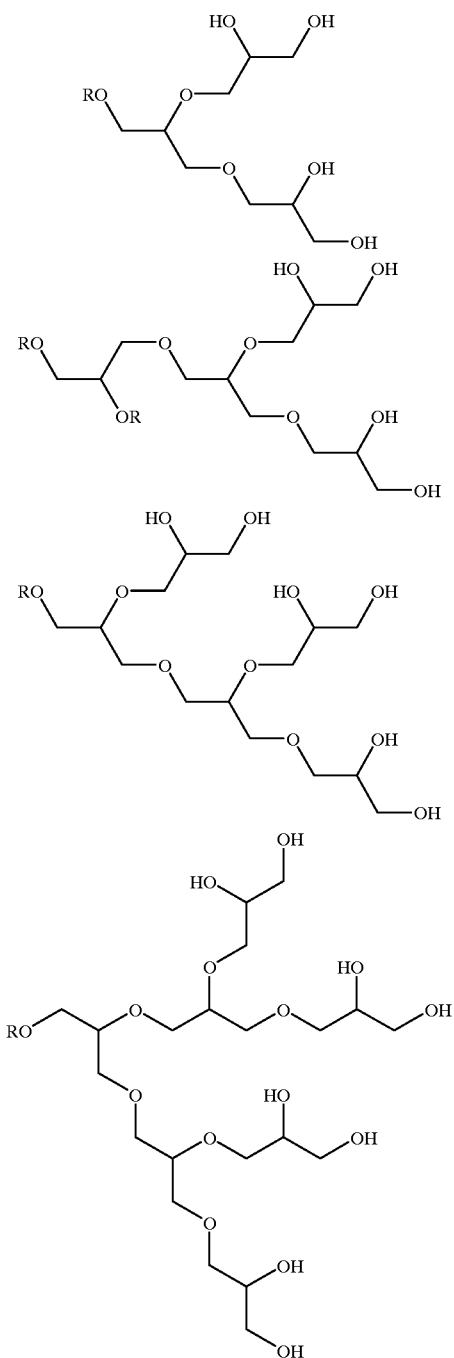

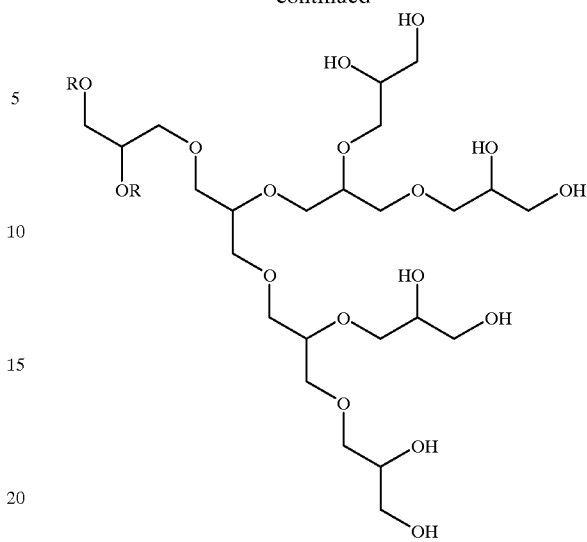

The process for synthesizing the polyglycerol alkyl ether of the present invention is not particularly limited. The polyglycerol alkyl ether can be similarly obtained as the polyether-polyol compound except for using an alkyl ether of the glycerol or polyglycerol as a starting substance in place of the glycerol or polyglycerol during the preparation of the polyether-polyol compound of the present invention.

The process for preparing a raw material alkyl ether of the glycerol or polyglycerol is not particularly limited, and any of commercially available natural products and synthetic products can be utilized. The chain length of the alkyl moiety is not particularly limited, and can be properly selected in accordance with its purposes. For instance, those in a linear or branched form having preferably 6 to 30 carbon atoms, more preferably 8 to 22 carbon atoms can be utilized.

The HLB of the polyglycerol alkyl ether of the present invention is not particularly limited, and those in accordance with their purposes can be utilized. Those esters having an HLB of 5 or more, preferably an HLB of 8 or more, more preferably an HLB of 10 or more, are recommendable, from the viewpoint of dispersibility in water. This HLB can be determined by using a known lipophilic surfactant and a fat or oil. In addition, the HLB can be calculated from the following equation:

$$HLB = 7 + 11.7 \log(MW/MO),$$

wherein MW is a molecular weight of the hydrophilic group moiety of the ether, and MO is a molecular weight of the lipophilic group moiety of the ether.

Further, the present invention provides an ester prepared by the process comprising reacting the polyether-polyol compound or polyglycerol alkyl ether described above with a fatty acid.

The ester of the present invention is obtained by esterifying the polyether-polyol compound or polyglycerol alkyl ether with a fatty acid by an appropriate method. The kinds of the fatty acid and the degree of esterification are not particularly limited. The fatty acid, such as a saturated or unsaturated, linear or branched fatty acid, or a fatty acid containing hydroxyl group in its molecule, each preferably having 6 to 30 carbon atoms, more preferably having 8 to 22 carbon atoms, and a mixture thereof in a given molar ratio in accordance with its purposes can be used in accordance with its purposes. The polyether-polyol compound or polyglycerol alkyl ether can be usually esterified with the fatty acid by heating the reaction mixture to a temperature of 200° C. or more with removing water in the presence of an acidic or alkali catalyst, or in the absence of the catalyst. In addition, in place of the fatty acid, a derivative of the fatty acid, such as a corresponding acid chloride, acid hydride and methyl ester of the fatty acid can be utilized. Also, when an appropriate organic solvent such as pyridine is used, the reaction can be achieved at an even lower temperature. The ester thus obtained can be purified in accordance with its purposes. The purification can be carried out by distillation techniques such as distillation under reduced pressure, molecular distillation, or vapor distillation. Besides the distillation techniques, extraction with an organic solvent, fractionation, or chromatography separation on a column packed with a synthetic adsorbent or gel filtration agent can be utilized. In addition, a selective esterification can be carried out by using an enzyme in a system containing very small amount of water.

The HLB of the ester of the present invention is not particularly limited, and those in accordance with their purposes can be utilized. Those esters having an HLB of 5 or more, preferably 8 or more, more preferably 10 or more are recommendable, from the viewpoint of dispersibility in water. This HLB can be determined by using a known lipophilic surfactant and a fat or oil. In addition, the HLB can be calculated from the following equation:

$$HLB = 20 \times (1 - S/A),$$

wherein S is a saponification value of the ester, and A is a neutralization value of the fatty acid used.

Each of the polyether-polyol compound, the polyglycerol alkyl ether and the ester of the present invention can be used alone. In addition, each of these can be utilized in the form of a composition by adding and mixing each of them with other substances in accordance with its purposes. The composition can be favorably used as foods, cosmetics and the like for the purposes of emulsification, solubilization, dispersion, washing, foaming, defoaming, permeation, antibacterial action, and the like. For instance, the composition can be utilized as follows. In the field of foods, the composition can be applied to instant foods such as instant noodles, retort pouch foods, canned foods, microwave-cooking foods, instant soups and miso soups, and freeze-dried foods; beverages such as soft drinks, fruits juices, vegetable juices, soya milk beverages, coffee beverages, tea beverages, powdered drinks, concentrate beverages, nutritious beverages, and alcoholic beverages; flour products such as bread, pastas, noodles, cake mix, deep frying powder, and bread crumbs; confectioneries such as caramel, candies, chewing gums, chocolate, cookies, biscuits, cakes, pies, snacks, crackers, Japanese sweets, and desert confectioneries; seasonings such as sauces, tomato-based seasonings, flavor seasonings, culinary mix, gravy sauces, dressings, clear soups, and roux for curry sauce and stew; fats and oils such as processed fats and oils, butter, margarine, and mayonnaise; milk products such as milk beverages, yogurts, lactobacilli beverages, ice creams, and creams; marine processed products such as frozen foods, hams and sausages made of fish, and marine pastes (chikuwa and kamaboko); livestock processed products such as livestock ham and sausages; agricultural processed products such as agricultural canned foods, jams and marmalades, pickles, cooked beans, and cereals; nutritional foods; emulsifiers for foods; and the like. Especially when utilized in foods, in addition to those applications, the composition can be used in the modifications of starches, proteins and fats and oils. In addition, in the field of the cosmetics, the composition can be applied to detergents such as soaps, cleansing lotions, shampoos, rinses, raw materials for surfactants; basic cosmetics such as lotions, milky lotions, moisturizers, skin creams, facial packs, hair tonics, and hair creams; finishing cosmetics such as lipsticks, eye shadows, set lotions, and hairdressings; fragrances such as perfumes and lotions; oral use cosmetics such dentifrice and mouthwash; and the like. Further, the composition can be applied to pharmaceuticals and industrial purposes. In the field of industry, the composition can be used for applications of dispersion of a filler, a pigment, or a paint in a resin, a cross-linking agent for a resin, a swelling agent, a surfactant, a dyeing aid, a paper modifier, a preventive for triboelectric charging, and a plasticizer. In the field of food industry, the composition can be used as cleaning agents for equipments, processing aids, detergents for vegetables and fruits; and the like. The applications of the composition are not limited to those listed above.

Further, the polyether-polyol compound, the polyglycerol alkyl ether, and the ester of the present invention can be, for instance, used as a surfactant preparation by mixing with other surfactants. Other surfactants which can be used for this purpose include natural occurring surfactants such as lecithin, saponin, proteins, and polysaccharides; those modified by acting the surfactant with an enzyme; and those chemically synthesized. The chemically synthesized surfactants can be roughly classified into ionic surfactants and nonionic surfactants. The ionic surfactants can be further classified into anionic surfactants, cationic surfactants and amphoteric surfactants. Examples of the anionic surfactants include aliphatic monocarboxylates, polyoxyethylene alkyl ether carboxylates, N-acyl sarcosine salts, N-acyl glutamate, dialkylsulfosuccinates, alkanesulfonates, alpha-olefinsulfonates, linear or branched alkylbenzenesulfonates, formaldehyde condensates of naphthalenesulfonates, alkylnaphthalenesulfonates, N-methyl-N-acyltaurine salts, alkylsulfates, polyoxyethylene alkyl ether sulfates, salts of fat and oil sulfuric acid esters, alkylphosphates, polyoxyethylene alkyl ether phosphates, polyoxyethylene alkylphenyl ether phosphates, and the like. Examples of the cationic surfactants include alkylamine salts, alkyltrimethylammonium chlorides, bromides or iodides, dialkyldimethylammonium chlorides, bromides or iodides, alkyl benzalkonium chloride. Examples of amphoteric surfactants include alkyl betaines, fatty acid amide propyl betaines, 2-alkyl-N-carboxymethyl-N-hydroxyethylimidazolinium betaines, alkyl- or dialkyldiethylenetriaminoacetic acids, alkylamine oxides. Examples of the nonionic surfactants include glycerol fatty acid esters, sorbitan fatty acid esters, sucrose fatty acid esters, propylene glycol fatty acid esters, polyoxyethylene alkyl ethers, polyoxyethylene alkylphenyl ethers, polyoxyethylene polyoxypropylene glycols, fatty acid polyethylene glycols, fatty acid polyoxyethylene sorbitans, fatty acid alkanolamides, and the like. The surfactants are not limited to those listed above. Especially in the field of foods, surfactants which are included in the glycerol fatty acid esters include conventional linear polyglycerol fatty acid esters, glycerol fatty acid esters, glycerol acetic acid ester, lactic acid esters of monoglyceride, citric acid esters of monoglyceride, succinic acid esters of monoglyceride, diacetyl tartaric acid esters of monoglyceride, polyglycerol poly-recinoleates, without being limited thereto. Also, other components can be added to each of the polyether-polyol compound, the polyglycerol alkyl ether, and the ester of the present invention, so that the handling of the mixture can be facilitated. For instance, in order to lower the viscosity of the product, one or more solvents selected from the group consisting of water, ethanol, propylene glycol, glycerol, linear polyglycerols, liquid sugars, and fats and oils can be added to the composition of the present invention. In addition, a polysaccharide such as lactose or dextrin or a protein such as caseinate can be added to the composition, and then powderized. Further, other components constituting a final product can be added to each of the polyether-polyol compound, the polyglycerol alkyl ether, and the ester of the present invention to give an intermediary product. For instance, each of the polyether-polyol compound, the polyglycerol alkyl ether, and the ester of the present invention can be mixed with an oil-soluble vitamin such as vitamin E, an oil-soluble pigment such as β-carotene, an oil-soluble bioactive substance such as a higher unsaturated fatty acid and an oil-soluble perfume, to give each product of a water-dispersible oil-soluble vitamin, a water-dispersible oil-soluble pigment, a water-dispersible bioactive substance, or a water-dispersible oil-soluble perfume.

EXAMPLES

Next, the present invention will be described in detail by means of the following Examples, without intending to limit the present invention thereto.

Example A1

A one-liter four-necked flask equipped with a stirrer, a reflux condenser and a thermometer was charged with 100 g of glycerol, 310 g of a 50% by weight aqueous sodium hydroxide and 310 ml of allyl chloride, and the mixture was stirred at 40° C. for 10 hours. Water was added to the product, with stirring, and thereafter the mixture was allowed to stand to separate into aqueous and organic layers. After removing the aqueous layer, the organic layer was concentrated with heating under reduced pressure, to give 196 g of a residue. Separately, a 3-liter flask was charged with one liter of formic acid and 500 ml of a 35% by weight aqueous hydrogen peroxide, and to this flask was gradually added the previous reaction mixture, and the mixture was allowed to react at 45° C. for 8 hours. Subsequently, formic acid and water were distilled off with heating under reduced pressure, and thereafter 500 ml of a 10% by weight aqueous sodium hydroxide was added to the resulting residue, and the mixture was stirred at 40° C. for 5 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 205 g of tetraglycerol.

A part of this compound was analyzed by mass spectrometer. As a result, the compound was found to have a molecular weight of 314 and a compositional formula of $C_{12}H_{26}O_9$, which was perfectly identical with the theoretical value of the tetraglycerol. The infrared absorption spectroscopy of this compound was determined. As a result, absorptions of ether bonds and hydroxyl groups were detected. Also, a 100-ml four-necked flask equipped with a stirrer, a reflux condenser and a thermometer was charged with 1 g of the resulting tetraglycerol, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 1.3 g of a residue. The infrared absorption spectroscopy of the resulting compound was determined. As a result, no absorption by hydroxyl group was found. In addition, this acetal was analyzed by mass spectrometer. The compound was found to have a molecular weight of 434 and a compositional formula $C_{21}H_{38}O_9$, which was perfectly identical to theoretical value. It was confirmed from these results that the tetraglycerol has three partial structures of 1,2-diol.

Example A2

A one-liter four-necked flask equipped with a stirrer, a reflux condenser and a thermometer was charged with 100 g of diglycerol (manufactured by Solvay, purity: 94%), 240 g of a 50% by weight aqueous sodium hydroxide and 245 ml of allyl chloride, and the mixture was stirred at 40° C. for 10 hours. Water was added to the product, with stirring, and thereafter the mixture was allowed to stand to separate into aqueous and organic layers. After removing the aqueous layer, the organic layer was concentrated with heating under reduced pressure, to give 165 g of a residue. Separately, a 3-liter flask was charged with 800 ml of formic acid and 400 ml of a 35% by weight aqueous hydrogen peroxide, and to this flask was gradually added the previous reaction mixture. The temperature of the mixture was raised to 45° C., and the mixture was allowed to react at 45° C. for 8 hours. Subsequently, formic acid and water were distilled off with heating under reduced pressure, and thereafter 500 ml of a 10% by weight aqueous sodium hydroxide was added to the resulting residue, and the mixture was stirred at 40° C. for 5 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 183 g of hexaglycerol.

A part of this compound was analyzed by mass spectrometer. As a result, the compound was found to have a molecular weight of 462 and a compositional formula of $C_{18}H_{38}O_{13}$, which was perfectly identical with the theoretical value of the hexaglycerol. The infrared absorption spectroscopy of this compound was determined. As a result, absorptions of ether bonds and hydroxyl groups were detected. Also, a 100-ml four-necked flask equipped with a stirrer, a reflux condenser and a thermometer was charged with 1 g of the resulting hexaglycerol, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 1.3 g of a residue. The infrared absorption spectroscopy of the resulting compound was determined. As a result, no absorption by hydroxyl group was found. In addition, this acetal was analyzed by mass spectrometer. The compound was found to have a molecular weight of 622 and a compositional formula $C_{30}H_{54}O_{13}$, which was perfectly identical to theoretical value. It was confirmed from these results that the hexaglycerol has four partial structures of 1,2-diol.

Example A3

A 500 ml four-necked flask equipped with a stirrer, a reflux condenser and a thermometer was charged with 50 g of tetraglycerol obtained in Example A1, 100 g of a 50% by weight aqueous sodium hydroxide and 100 ml of allyl chloride, and the mixture was stirred at 40° C. for 15 hours. Water was added to the product, with stirring, and thereafter the mixture was allowed to stand to separate into aqueous and organic layers. After removing the aqueous layer, the organic layer was concentrated with heating under reduced pressure, to give 69 g of a residue. Separately, a one-liter flask was charged with 400 ml of formic acid and 200 ml of a 35% by weight aqueous hydrogen peroxide, and to this flask was gradually added the previous reaction mixture. The temperature of the mixture was raised to 45° C., and the mixture was allowed to react at 45° C. for 10 hours. Subsequently, formic acid and water were distilled off with heating under reduced pressure, and thereafter 200 ml of a 10% by weight aqueous sodium hydroxide was added to the resulting residue, and the mixture was stirred at 40° C. for 10 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 71 g of decaglycerol.

A part of this compound was analyzed by mass spectrometer. As a result, the compound was found to have a molecular weight of 758 and a compositional formula of $C_{30}H_{62}O_{21}$, which was perfectly identical with the theoretical value of the decaglycerol. The infrared absorption spectroscopy of this compound was determined. As a result, absorptions of ether bonds and hydroxyl groups were detected. Also, a 100-ml four-necked flask equipped with a stirrer, a reflux condenser and a thermometer was charged with 1 g of the resulting decaglycerol, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 1.3 g of a residue. The infrared absorption spectroscopy of the resulting compound was determined. As a result, no absorption by hydroxyl group was found. In addition, this acetal was analyzed by mass spectrometer. The compound was found to have a molecular weight of 998 and a compositional formula $C_{48}H_{86}O_{21}$, which was perfectly identical to theoretical value. It was confirmed from these results that the decaglycerol has six partial structures of 1,2-diol.

Example A4

A 500 ml four-necked flask equipped with a stirrer, a reflux condenser and a thermometer was charged with 50 g of the polyglycerol obtained in Comparative Example A2, 120 g of a 50% by weight aqueous sodium hydroxide and 150 ml of allyl chloride, and the mixture was stirred at 40° C. for 15 hours. Water was added to the product, with stirring, and thereafter the mixture was allowed to stand to separate into aqueous and organic layers. After removing the aqueous layer, the organic layer was concentrated with heating under reduced pressure, to give 71 g of a residue. Separately, a one-liter flask was charged with 400 ml of formic acid and 200 ml of a 35% by weight aqueous hydrogen peroxide, and to this flask was gradually added the previous reaction mixture. The temperature of the mixture was raised to 45° C., and the mixture was allowed to react at 45° C. for 10 hours. Subsequently, formic acid and water were distilled off with heating under reduced pressure, and thereafter 200 ml of a 10% by weight aqueous sodium hydroxide was added to the resulting residue, and the mixture was stirred at 40° C. for 10 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 73 g of a polyglycerol.

Also, a 100-ml four-necked flask equipped with a stirrer, a reflux condenser and a thermometer was charged with 1 g of the resulting polyglycerol, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 1.2 g of a residue. This acetal was acetylated with acetic anhydride and pyridine, and thereafter analyzed by gas chromatographic mass spectrometer. As a result, it was found that the compound was composed of the plural kinds of polyglycerol components in branched forms and their compositional ratio is as shown in the following table.

TABLE A1

| Degree of Polymerization | Content (%) | Molecular Weight (found value) | Molecular Weight (theoretical value) |
|---|---|---|---|
| 4 | 22.7 | 434 | 434 |
| 5 | 0 | — | 550 |
| 6 | 28.6 | 622 | 622 |
| 7 | 0 | — | 738 |
| 8 | 16.2 | 810 | 810 |
| 9 | 0 | — | 926 |
| 10 | 18.7 | 998 | 998 |
| 11 | 0 | — | 1114 |
| 12 | 13.9 | 1186 | 1186 |

Comparative Example A1

A five-liter four-necked flask equipped with a stirrer, a gas-discharging tube and a thermometer was charged with 4000 g of a glycerol and 40 g of a 50% by weight aqueous sodium hydroxide. The mixture was heated to 240° C. with removing water from the system at a pressure of 100 Torr under nitrogen gas stream, and the mixture was kept at 240° C. for 13 hours, to give 2460 g of a polyglycerol reaction mixture. The reaction mixture was decolorized with activated charcoal, and thereafter the mixture was purified with an ion exchange resin. Water was removed under reduced pressure, to give 2430 g of a polyglycerol. A part of the resulting polyglycerol was taken, and its hydroxyl value thereof was determined. As a result, the hydroxyl value was found to be 1080, which corresponded to a tetraglycerol in a linear form. Also, a 100-ml four-necked flask equipped with a stirrer, a reflux condenser and a thermometer was charged with 1 g of the resulting polyglycerol, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 0.8 g of a residue. The infrared absorption spectroscopy of the resulting compound was determined. As a result, absorptions by hydroxyl groups were detected. In addition, this acetal was acetylated with acetic anhydride and pyridine, and thereafter analyzed by gas chromatographic mass spectrometer. As a result, the polyglycerol component in a branched form was not detected.

Comparative Example A2

A five-liter four-necked flask equipped with a stirrer, a gas-discharging tube and a thermometer was charged with 4000 g of a glycerol and 40 g of a 50% by weight aqueous sodium hydroxide. The mixture was heated to 240° C. with removing water from the system at a pressure of 100 Torr under nitrogen gas stream, and the mixture was kept at 240° C. for 48 hours, to give 2315 g of a polyglycerol reaction mixture. The reaction mixture was decolorized with activated charcoal, and thereafter the mixture was purified with an ion exchange resin. Water was removed under reduced pressure, to give 2282 g of a polyglycerol. A part of the resulting polyglycerol was taken, and its hydroxyl value thereof was determined. As a result, the hydroxyl value was found to be 896, which corresponded to a decaglycerol in a linear form. Also, a 100-ml four-necked flask equipped with a stirrer, a reflux condenser and a thermometer was charged with 1 g of the resulting polyglycerol, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 0.7 g of a residue. The infrared absorption spectroscopy of the resulting compound was determined. As a result, absorptions by hydroxyl groups were detected. In addition, this acetal was acetylated with acetic anhydride and pyridine, and thereafter analyzed by gas chromatographic mass spectrometer. As a result, the polyglycerol component in a branched form was not detected.

Example B1

A 3-liter four-necked flask equipped with a stirrer, a nitrogen inlet tube and a thermometer was charged with 760 g of glycerol and 4 g of sodium hydroxide, and the mixture was dehydrated at 120° C. under reduced pressure for 1 hour. Having changed the pressure back to normal pressure, 400 g of glycidyl dodecyl ether was added dropwise over a period of 2 hours to the dehydrated mixture at 160° C. under nitrogen stream, and thereafter the mixture was stirred for 8 hours. The resulting reaction mixture was purified by molecular distillation, to give 212 g of diglycerol dodecyl ether. A one-liter four-necked flask equipped with a stirrer, a nitrogen inlet tube and a thermometer was charged with 200 g of the diglycerol dodecyl ether, 84 g of sodium hydroxide and 230 g of allyl chloride, and the mixture was stirred at 40° C. under nitrogen gas stream for 10 hours. Water was added to the product, with stirring, and thereafter the mixture was allowed to stand to separate into aqueous and organic layers. After removing the aqueous layer, the organic layer was concentrated with heating under reduced pressure, to give 196 g of a residue. Separately, a 3-liter flask was charged with 900 ml of formic acid and 450 ml of a 35% by weight aqueous hydrogen peroxide, and to this flask was gradually added the previous reaction mixture, and the mixture was allowed to react at 45° C. for 8 hours. Subsequently, formic acid and water were distilled off with heating under reduced pressure, and 500 ml of a 10% by weight aqueous sodium hydroxide was added to the resulting residue, and the mixture was stirred at 40° C. for 5 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 216 g of pentaglycerol dodecyl ether.

A part of this compound was analyzed by mass spectrometer. As a result, the compound was found to have a molecular weight of 556 and a compositional formula of $C_{27}H_{56}O_{11}$, which was perfectly identical with the theoretical value of the pentaglycerol dodecyl ether. Also, a 100-ml four-necked flask equipped with a stirrer, a reflux condenser and a thermometer was charged with 1 g of the resulting pentaglycerol dodecyl ether, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 1.3 g of a residue. The infrared absorption spectroscopy of the resulting compound was determined. As a result, no absorption by hydroxyl group was found. In addition, this acetal was analyzed by mass spectrometer. The compound was found to have a molecular weight of 676 and a compositional formula $C_{36}H_{68}O_{11}$, which was perfectly identical to theoretical value. It was confirmed from these results that the tetraglycerol has three partial structures of 1,2-diol. The HLB of the pentaglycerol dodecyl ether is 10.7.

Example B2

A 3-liter four-necked flask equipped with a stirrer, a nitrogen inlet tube and a thermometer was charged with 600 g of glycerol and 3 g of sodium hydroxide, and the mixture was dehydrated at 120° C. under reduced pressure for 1 hour. Having changed the pressure back to normal pressure, 400 g of glycidyl octadecanoyl ether was added dropwise to the dehydrated mixture over a period of 2 hours at 160° C. under nitrogen stream, and thereafter the mixture was stirred for 8 hours. The resulting reaction mixture was purified by molecular distillation, to give 192 g of diglycerol octadecanoyl ether. A one-liter four-necked flask equipped with a stirrer, a nitrogen inlet tube and a thermometer was charged with 180 g of the diglycerol octadecanoyl ether, 60 g of sodium hydroxide and 165 g of allyl chloride, and the mixture was stirred at 40° C. under nitrogen gas stream for 10 hours. Water was added to the product, with stirring, and thereafter the mixture was allowed to stand to separate into aqueous and organic layers. After removing the aqueous layer, the organic layer was concentrated with heating under reduced pressure, to give 208 g of a residue. Separately, a 3-liter flask was charged with 900 ml of formic acid and 450 ml of a 35% by weight aqueous hydrogen peroxide, and to this flask was gradually added the previous reaction mixture, and the mixture was allowed to react at 45° C. for 8 hours. Subsequently, formic acid and water were distilled off with heating under reduced pressure, and 500 ml of a 10% by weight aqueous sodium hydroxide was added to the resulting residue, and the mixture was stirred at 40° C. for 5 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 220 g of pentaglycerol octadecanoyl ether. A part of this compound was analyzed by mass spectrometer. As a result, the compound was found to have a molecular weight of 640 and a compositional formula of $C_{33}H_{68}O_{11}$, which was perfectly identical with the theoretical value of the pentaglycerol octadecanoyl ether. Also, a 100-ml four-necked flask equipped with a stirrer, a reflux condenser and a thermometer was charged with 1 g of the resulting pentaglycerol octadecanoyl ether, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 1.2 g of a residue. The infrared absorption spectroscopy of the resulting compound was determined. As a result, no absorption by hydroxyl group was found. In addition, this acetal was analyzed by mass spectrometer. The compound was found to have a molecular weight of 760 and a compositional formula $C_{42}H_{80}O_{11}$, which was perfectly identical to theoretical value. It was confirmed from these results that the tetraglycerol has three partial structures of 1,2-diol. The HLB of the pentaglycerol octadecanoyl ether is 8.8.

Example B3

A one-liter four-necked flask equipped with a stirrer, a nitrogen inlet tube and a thermometer was charged with 200 g of glycerol dodecyl ether, 77 g of sodium hydroxide and 294 g of allyl chloride, and the mixture was stirred at 40° C. under nitrogen gas stream for 10 hours. Water was added to the product, with stirring, and thereafter the mixture was allowed to stand to separate into aqueous and organic layers. After removing the aqueous layer, the organic layer was concentrated with heating under reduced pressure, to give 235 g of a residue. Separately, a 3-liter flask was charged with one liter of formic acid and 500 ml of a 35% by weight aqueous hydrogen peroxide, and to this flask was gradually added the previous reaction mixture, and the mixture was allowed to react at 45° C. for 8 hours. Subsequently, formic acid and water were distilled off with heating under reduced pressure, and thereafter 500 ml of a 10% by weight aqueous sodium hydroxide was added to the resulting residue, and the mixture was stirred at 40° C. for 5 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 251 g of triglycerol dodecyl ether.

A one-liter four-necked flask equipped with a stirrer, a nitrogen inlet tube and a thermometer was charged with 200 g of the resulting triglycerol dodecyl ether, 88 g of sodium hydroxide and 300 g of allyl chloride, and the mixture was stirred at 40° C. under nitrogen gas stream for 10 hours. Water was added to the product, with stirring, and thereafter the mixture was allowed to stand to separate into aqueous and organic layers. After removing the aqueous layer, the organic layer was concentrated with heating under reduced pressure, to give 248 g of a residue. Separately, a 3-liter flask was charged with one liter of formic acid and 500 ml of a 35% by weight aqueous hydrogen peroxide, and to this flask was gradually added the previous reaction mixture, and the mixture was allowed to react at 45° C. for 8 hours. Subsequently, formic acid and water were distilled off with heating under reduced pressure, and thereafter 500 ml of a 10% by weight aqueous sodium hydroxide was added to the resulting residue, and the mixture was stirred at 40° C. for 5 hours. The reaction mixture was neutralized with a 10% by weight hydrochloric acid, and thereafter thermally dehydrated under reduced pressure. Water was added to the resulting residue, and the mixture was desalted through a cationic exchange resin and an anionic exchange resin. The desalted product was dehydrated under reduced pressure, to give 261 g of heptaglycerol dodecyl ether. A part of this compound was analyzed by mass spectrometer. As a result, the compound was found to have a molecular weight of 705 and a compositional formula of $C_{33}H_{69}O_{15}$, which was perfectly identical with the theoretical value of the heptaglycerol dodecyl ether. Also, a 100-ml four-necked flask equipped with a stirrer, a reflux condenser and a thermometer was charged with 1 g of the resulting heptaglycerol dodecyl ether, 40 ml of dry acetone and 0.4 g of ferric chloride, and the mixture was stirred at 40° C. for 8 hours. After removing acetone under reduced pressure, 50 ml of diethyl ether was added to the residue and then rinsed with water. A diethyl ether layer was dried over anhydrous sodium sulfate, and thereafter the solvent was removed under reduced pressure, to give 1.3 g of a residue. The infrared absorption spectroscopy of the resulting compound was determined. As a result, no absorption by hydroxyl group was found. In addition, this acetal was analyzed by mass spectrometer. The compound was found to have a molecular weight of 865 and a compositional formula $C_{45}H_{85}O_{15}$, which was perfectly identical to theoretical value. It was confirmed from these results that the heptaglycerol dodecyl ether has four partial structures of 1,2-diol. The HLB of the heptaglycerol dodecyl ether is 12.4.

Comparative Example B1

A one-liter four-necked flask equipped with a stirrer, a nitrogen inlet tube and a thermometer was charged with 186 g of dodecyl alcohol and 9 g of sodium hydroxide. The mixture was then dehydrated with heating to 120° C. under reduced pressure. Next, 370 g of glycidol (5 times by mol against the dodecyl alcohol) was added dropwise at 120° C. over a period of 1 hour, and the mixture was stirred for additional 2 hours. Water was added to the resulting product, and the product was desalted through a cationic exchange resin and an anionic exchange resin. The desalted product was dehydrated under reduced pressure, to give 523 g of pentaglycerol dodecyl ether. A 1 g sample of the resulting product was taken, and subjected to acetal formation in the same manner as in Example B1. The infrared absorption spectroscopy of the resulting product was determined. As a result, an absorption by hydroxyl group was detected. It was confirmed from these results that the pentaglycerol dodecyl ether has hydroxyl group other than the structure of 1,2-diol or 1,3-diol.

Comparative Example B2

Two-hundred and seventy grams of octadecanoyl alcohol, 370 g of glycidol (5 times by mol against the octadecanoyl alcohol) and 9 g of sodium hydroxide were reacted and purified in the same manner as in Comparative Example B1, to give 598 g of pentaglycerol octadecanoyl ether. A 1 g sample of the resulting product was taken, and subjected to acetal formation in the same manner as in Example B1. The infrared absorption spectroscopy of the resulting product was determined. As a result, an absorption by hydroxyl group was detected. It was confirmed from these results that the pentaglycerol octadecanoyl ether has hydroxyl group other than the structure of 1,2-diol or 1,3-diol.

Comparative Example B3

One-hundred and eighty-six grams of dodecyl alcohol, 518 g of glycidol (7 times by mol against the dodecyl alcohol) and 9 g of sodium hydroxide were reacted and purified in the same manner as in Comparative Example B1, to give 633 g of heptaglycerol dodecyl ether. A 1 g sample of the resulting product was taken, and subjected to acetal formation in the same manner as in Example B1. The infrared absorption spectroscopy of the resulting product was determined. As a result, an absorption by hydroxyl group was detected. It was confirmed from these results that the heptaglycerol dodecyl ether has hydroxyl group other than the structure of 1,2-diol or 1,3-diol.

Test Example B1

The detergency was determined for each of surfactants, the pentaglycerol dodecyl ether obtained in Example B1 and the pentaglycerol dodecyl ether obtained in Comparative Example B1, in accordance with *Gosei Senzai Shikenhou* (*Testing Method for Synthetic Detergent*) (published by Japanese Industrial Standards Committee, JIS K3362, revised Feb. 1, 1990) by a detergency tester. Here, the test was carried out at a temperature of 25° C. with a concentration of each surfactant of 0.03% by weight. The results, which are expressed by the removal percentage of the model fat and oil stains, are shown in Table B1.

TABLE B1

| Surfactant | Removal Percentage (%) |
|---|---|
| Pentaglycerol Dodecyl Ether Obtained in Example B1 | 99 |
| Pentaglycerol Dodecyl Ether Obtained in Comparative Example B1 | 61 |

It is clear from the results in Table B1 that the pentaglycerol dodecyl ether obtained in Example B1 has more excellent detergency as compared to the pentaglycerol dodecyl ether obtained in Comparative Example B1.

Test Example B2

The emulsion stability was determined for each of surfactants, the pentaglycerol octadecanoyl ether obtained in Example B2 and the pentaglycerol octadecanoyl ether obtained in Comparative Example B2, in accordance with the following procedures. Specifically, 2.5 g of each surfactant was added to 250 g of water, and the mixture was heated to 60° C. With stirring with a homomixer at 3000 rpm, 250 g of rapeseed oil separately heated to 60° C. was gradually added to the resulting mixture, and thereafter the mixture was stirred at 10000 rpm for 3 minutes, to give an emulsion. This emulsion was stored at 60° C. for 24 hours. The emulsion state of the pentaglycerol octadecanoyl ether obtained in Example B2 was compared with that of the pentaglycerol octadecanoyl ether obtained in Comparative Example B2. As a result, while no separated water was found for the one containing the pentaglycerol octadecanoyl ether obtained in Example B2, 23% separated water was found for the one containing the pentaglycerol octadecanoyl ether obtained in Comparative Example B2. It is clear from the above results that the pentaglycerol octadecanoyl ether obtained in Example B2 has more excellent emulsion stability as compared to the pentaglycerol octadecanoyl ether obtained in Comparative Example B2.

Test Example B3

The solubilizing capacity was determined for each of surfactants, the heptaglycerol dodecyl ether obtained in Example B3 and the heptaglycerol dodecyl ether obtained in Comparative Example B3, in accordance with the following procedures. Each of ten test tubes was charged with dl-α-tocopherol with varying its amount in the range of 0 to 50 mg, and 10 ml of 1% by weight solution of the heptaglycerol dodecyl ether obtained in Example B3 was added thereto. The mixture was stirred with a homogenizer for 10 seconds, and thereafter the transmittance at 650 nm was determined. The results are plotted in a graph, taking the amount of the tocopherol as the abscissa, and the transmittance as the ordinate. The amount of the tocopherol which corresponds to the transmittance of 90% was determined. Similarly, a test was carried out with the heptaglycerol dodecyl ether obtained in Comparative Example B3. It is found from the comparison of the results that in contrast to the fact that 45 mg of the heptaglycerol dodecyl ether obtained in Example B3 can be solubilized for the transmittance to be lowered to 90%, only 5 mg or less of the heptaglycerol dodecyl ether obtained in Comparative Example B3 can be solubilized, whereby showing that the heptaglycerol dodecyl ether obtained in Example B3 is more excellent in the solubilizing capacity as compared to that of the heptaglycerol dodecyl ether obtained in Comparative Example B3.

Test Example B4

Each of cleansing creams, inventive product A and comparative product B, was prepared in accordance with the composition as shown in Table B2.

TABLE B2

|  | A | B |
|---|---|---|
| Liquid Paraffin | 55 | 55 |
| Glycerol | 37 | 37 |
| 1,3-Butylene Glycol | 2 | 2 |
| Purified Water | 2 | 2 |
| Pentaglycerol Dodecyl Ether Obtained in Example B1 | 2 |  |
| Pentaglycerol Dodecyl Ether Obtained in Comparative Example B1 |  | 2 |

Units: % by weight

The liquid paraffin was added dropwise with mixing each surfactant, glycerol, 1,3-butylene glycol and purified water at 60° C. The resulting composition was stored at 60° C. for 10 days. As a result, the mixture was separated into two layers in the composition B, in contrast to no property changes in the composition A. It is clear from above that the pentaglycerol dodecyl ether obtained in Example B1 is more excellent in properties, as compared to that of the pentaglycerol dodecyl ether obtained in Comparative Example B1, when applied to cleansing cream.

As verified above, since the polyglycerol alkyl ether of the present invention is contained in the composition, the resulting composition can exhibit higher detergency, emulsion stability, and solubilizing capacity.

Example C1

A 200-ml four-necked flask equipped with a stirrer, a thermometer, a nitrogen inlet tube and a gas-discharging tube was charged with 60.0 g of the tetraglycerol obtained in Example A1, 38.2 g of lauric acid and 0.4 g of sodium hydroxide, and the mixture was reacted at 230° C. for 2 hours under nitrogen gas stream, to give 93.3 g of tetraglycerol laurate (HLB=11.9). In addition, similarly, the esterification reaction was carried out by using 54.3 g of stearic acid in place of lauric acid, to give 106.3 g of tetraglycerol stearate (HLB=10.2).

Example C2

A 100-ml four-necked flask equipped with a stirrer, a thermometer, a nitrogen inlet tube and a gas-discharging tube was charged with 30.0 g of the decaglycerol obtained in Example A3, 8.0 g of lauric acid and 0.04 g of sodium hydroxide, and the mixture was reacted at 230° C. for 2 hours under nitrogen gas stream, to give 36.0 g of decaglycerol laurate (HLB=15.7). In addition, similarly, the esterification reaction was carried out by using 11.5 g of stearic acid in place of lauric acid, to give 39.5 g of decaglycerol stearate (HLB=14.4).

Example C3

A 200-ml four-necked flask equipped with a stirrer, a thermometer, a nitrogen inlet tube and a gas-discharging tube was charged with 60.0 g of the polyglycerol obtained in Example A4, 22.5 g of stearic acid and 0.1 g of sodium hydroxide, and the mixture was reacted at 230° C. for 2 hours under nitrogen gas stream, to give 78.0 g of a mixture of plural kinds of polyglycerol stearate in branched form (HLB=14.0).

Comparative Example C1

A one-liter four-necked flask equipped with a stirrer, a thermometer, a nitrogen inlet tube and a gas-discharging tube was charged with 400.0 g of the tetraglycerol obtained in Comparative Example A1, 255.0 g of lauric acid and 0.7 g of sodium hydroxide, and the mixture was reacted at 230° C. for 2 hours under nitrogen gas stream, to give 628.8 g of tetraglycerol laurate (HLB=11.9). In addition, similarly, the esterification reaction was carried out by using 362 g of stearic acid in place of lauric acid, to give 723.9 g of tetraglycerol stearate (HLB=10.2).

Comparative Example C2

A one-liter four-necked flask equipped with a stirrer, a thermometer, a nitrogen inlet tube and a gas-discharging tube was charged with 400.0 g of the decaglycerol obtained in Comparative Example A2, 105.5 g of lauric acid and 0.5 g of sodium hydroxide, and the mixture was reacted at 230° C. for 2 hours under nitrogen gas stream, to give 470.1 g of decaglycerol laurate (HLB=15.7). In addition, similarly, the esterification reaction was carried out by using 150.0 g of stearic acid in place of lauric acid, to give 522.5 g of decaglycerol laurate (HLB=14.4).

Test Example C1

The interfacial tension of a 0.1% aqueous surfactant solution and corn oil at 40° C. was determined by a Wilhemy's method, for the tetraglycerol laurate and the tetraglycerol stearate each obtained in Example C1, and the tetraglycerol laurate and the tetraglycerol stearate obtained in Comparative Example C1. The results are shown in Table C1.

TABLE C1

| Name of Surfactant | Surface Tension (mN/m) |
| --- | --- |
| No Addition | 24.5 |
| Tetraglycerol Laurate Obtained in Example C1 | 2.1 |
| Tetraglycerol Stearate Obtained in Example C1 | 1.5 |

TABLE C1-continued

| Name of Surfactant | Surface Tension (mN/m) |
| --- | --- |
| Tetraglycerol Laurate Obtained in Comparative Example C1 | 15.4 |
| Tetraglycerol Stearate Obtained in Comparative Example C1 | 11.3 |

It is clear from the results in Table C1 that the tetraglycerol laurate and stearate in branched forms are more excellent in lowering the surface tension than the tetraglycerol laurate and stearate in linear forms.

Test Example C2

The emulsion ability was determined for each of surfactants, the tetraglycerol stearate obtained in Example C1, the decaglycerol stearate obtained in Example C2, the polyglycerol stearate obtained in Example C3, the tetraglycerol stearate obtained in Comparative Example C1 and the decaglycerol stearate obtained in Comparative Example C2, by the following procedures. Specifically, 2.5 g of each surfactant was added to 250 g of water, and the mixture was heated to 60° C. With stirring the mixture with a homomixer at 3000 rpm, 250 g of rapeseed oil separately heated to 60° C. was gradually added to the mixture, and thereafter the mixture was stirred at 10000 rpm for 3 minutes to give an emulsion. The emulsion state was compared after storing the emulsion at 60° C. for 24 hours. The emulsion state was evaluated by the following criteria:

Criteria

⊚: amount of water separated being 1% or less;

◯: amount of water separated being 10% or less and exceeding 1%;

Δ: amount of water separated being 30% or less and exceeding 10%; and x: emulsion corrupting (separation of oil droplets)

The results are shown in Table C2.

TABLE C2

| Name of Surfactant | Evaluation of Emulsion State |
| --- | --- |
| Tetraglycerol Stearate Obtained in Example C1 | ⊚ |
| Decaglycerol Stearate Obtained in Example C2 | ⊚ |
| Polyglycerol Stearate Obtained in Example C3 | ⊚ |
| Tetraglycerol Stearate Obtained in Comparative Example C1 | x |
| Decaglycerol Stearate Obtained in Comparative Example C2 | Δ |

It is clear from the results in Table C2 that the tetra- and decaglycerol stearate in branched forms and the mixture of plural kinds of polyglycerol stearates in branched forms are more excellent in the emulsion ability than the tetra- and decaglycerol stearates in linear forms.

Test Example C3

The detergency was determined for each of surfactants, the decaglycerol laurate obtained in Example C2 and the decaglycerol laurate obtained in Comparative Example C2, in accordance with *Gosei Senzai Shikenhou* (*Testing Method for Synthetic Detergent*) (published by Japanese Industrial Standards Committee, JIS K3362, revised Feb. 1, 1990) by a detergency tester. Here, the test was carried out at a temperature of 25° C. with a concentration of each surfactant of 0.03% by weight. The results, which are expressed by the removal percentage of the model fat and oil stains, are shown in Table C3.

TABLE C3

| Surfactant | Removal Percentage (%) |
|---|---|
| Decaglycerol Laurate Obtained in Example C2 | 99 |
| Decaglycerol Laurate Obtained in Comparative Example C2 | 55 |

It is clear from the results in Table C3 that the decaglycerol laurate in a branched form has more excellent detergency as compared to the decaglycerol laurate in a linear form.

Test Example C4

Three kinds of emulsion dressings, the inventive product A and the comparative products B and C were prepared in accordance with the composition shown in Table C4.

TABLE C4

| | A | B | C |
|---|---|---|---|
| Corn Oil | 65 | 65 | 65 |
| Acetic Acid | 15 | 15 | 15 |
| Table Salt | 2 | 2 | 2 |
| Water | 17 | 17 | 17 |
| Decaglycerol Stearate Obtained in Example C2 | 1 | | |
| Polyglycerol Stearate Obtained in Example C3 | | 1 | |
| Decaglycerol Stearate Obtained in Comparative Example C2 | | | 1 |

Unit: % by weight

Acetic acid, table salt and an emulsifying agent were added to water, and the mixture was heated to 60° C. with stirring with a homomixer at 5000 rpm, and corn oil separately heated to 60° C. was gradually added thereto. Thereafter, the mixture was emulsified at 10000 rpm for 5 minutes. Each of the emulsions A to C was stored at 40° C. for 5 days, and as a result, 34% by volume of the corn oil was separated in the composition C, in contrast to having completely no oil layer separation in the compositions A and B.

It is clear from the above results in Table C4 that the decaglycerol stearate in a branched form and the mixture of the plural kinds of polyglycerol stearates in branched forms are more excellent in lowering the oil-layer separability as compared with that of the decaglycerol stearate in a linear form.

Test Example C5

The cocoa beverages, the inventive product A and the comparative product B were prepared in accordance with the composition shown in Table C5.

TABLE C5

| | A | B |
|---|---|---|
| Cocoa Powder | 25 | 25 |
| Sugar | 60 | 60 |
| Lactose | 10 | 10 |
| Water | 4 | 4 |
| Decaglycerol Laurate Obtained in Example C2 | 1 | |
| Decaglycerol Laurate Obtained in Comparative Example C2 | | 1 |

Unit: % by weight

Each of the compositions A and B was mixed and thereafter granulated with a granulator. A 10 g sample of each composition was gently added to 40 ml of water, and the mixture was allowed to stand for 4 hours. Thereafter, the liquid was gently decanted, and the amount of the granules sedimented at the bottom of the granulator without dispersing the liquid mixture was determined. As a result, the amount of the granules was 0.2 g for the composition A and 1.8 g for the composition B.

It is clear from the above that the decaglycerol laurate in a branched form is more excellent in the emulsion stability as compared to the decaglycerol laurate in a linear form.

Test Example C6

Each of cleansing creams, inventive product A and comparative product B, was prepared in accordance with the composition as shown in Table C6.

TABLE C6

| | A | B |
|---|---|---|
| Liquid Paraffin | 55 | 55 |
| Glycerol | 37 | 37 |
| 1,3-Butylene Glycol | 2 | 2 |
| Purified Water | 2 | 2 |
| Tetraglycerol Laurate Obtained in Example C1 | 2 | |
| Tetraglycerol Laurate Obtained in Comparative Example C1 | | 2 |

Units: % by weight

The liquid paraffin was added dropwise with mixing each emulsifying agent, glycerol, 1,3-butylene glycol and purified water at 60° C. The resulting composition was stored at 60° C. for 10 days. As a result, the mixture was separated into two layers in the composition B, in contrast to no property changes in the composition A.

It is clear from above that the tetraglycerol laurate in a branched form is more excellent in lowering the two-layer separability, as compared to that of the tetraglycerol laurate in a linear form, when applied to cleansing cream.

What is claimed is:
1. A polyether-polyol compound represented by the compositional formula:

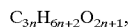

$C_{3n}H_{6n+2}O_{2n+1}$, wherein n is an integer of 6 or more,
wherein the polyether-polyol compound has a total number of 1,2-diol unit and 1,3-diol unit of $[(n/2)+1]$ in a case where n is an even number of 6 or more, or a total number of 1,2-diol unit and 1,3-diol unit of $[((n-1)/2)+1]$ and one hydroxyl group which is not involved in the units in a case where n is an odd number of 7 or more.

2. The polyether-polyol compound according to claim 1, which is prepared by the steps of carrying out an addition reaction of an allyl halide with glycerol or a polyglycerol having a degree of polymerization of two or more to give an allyl ether compound, and carrying out a reaction for converting a double bond contained in allyl group of the allyl ether compound to a single bond to introduce two hydroxyl groups.

3. A polyglycerol alkyl ether, wherein one or some of the hydroxyl groups in a polyglycerol are etherified with an alkyl group having 6 to 30 carbon atoms, wherein the polyglycerol is the polyether polyol compound of claim 1 or 2.

4. An ester prepared by the process comprising reacting the polyether-polyol compound of claim 1 or 2 or the polyglycerol alkyl ether of claim 3 with a fatty acid, wherein the fatty acid is a saturated or unsaturated, linear or branched fatty acid having 6 to 30 carbon atoms, or a fatty acid having 6 to 30 carbon atoms containing a hydroxyl group in its molecule, or a mixture thereof.

5. The ester according to claim 4, wherein the ester has an HLB of 5 or more, with HLB being calculated from the equation $HLB=20\times(1-S/A)$, wherein S is a saponification value of the ester and A is a neutralization value of the fatty acid used.

6. A composition comprising the polyether-polyol compound of claim 1 or 2, the polyglycerol alkyl ether of claim 3, or the ester of claim 4 or 5.

7. The composition according to claim 6, which is food.

8. The composition according to claim 6, which is cosmetic.

* * * * *